United States Patent
Prutchi

(10) Patent No.: US 12,083,348 B2
(45) Date of Patent: Sep. 10, 2024

(54) IMPLANTABLE CARDIOVERTER DEFIBRILLATOR (ICD) DEVICE WITH HIGH LONGEVITY

(71) Applicant: Impulse Dynamics NV, Willemstad (CW)

(72) Inventor: David Prutchi, Voorhees, NJ (US)

(73) Assignee: Impulse Dynamics NV, Willemstad (CW)

( * ) Notice: Subject to any disclaimer, the term of this patent is extended or adjusted under 35 U.S.C. 154(b) by 239 days.

(21) Appl. No.: 17/790,770

(22) PCT Filed: Jan. 5, 2021

(86) PCT No.: PCT/IB2021/050031
§ 371 (c)(1),
(2) Date: Jul. 5, 2022

(87) PCT Pub. No.: WO2021/137201
PCT Pub. Date: Jul. 8, 2021

(65) Prior Publication Data
US 2023/0041857 A1    Feb. 9, 2023

Related U.S. Application Data

(60) Provisional application No. 62/957,243, filed on Jan. 5, 2020.

(51) Int. Cl.
*A61N 1/39*    (2006.01)
*A61N 1/378*    (2006.01)

(52) U.S. Cl.
CPC ........... *A61N 1/378* (2013.01); *A61N 1/3956* (2013.01); *A61N 1/3975* (2013.01)

(58) Field of Classification Search
CPC ..... A61N 1/378; A61N 1/3956; A61N 1/3975
See application file for complete search history.

(56) References Cited

U.S. PATENT DOCUMENTS

| 5,405,363 A | 4/1995 | Kroll et al. |
| 5,957,956 A * | 9/1999 | Kroll ................. A61N 1/375 607/5 |

(Continued)

FOREIGN PATENT DOCUMENTS

| CN | 106093795 | 11/2016 |
| CN | 10678713 | 5/2017 |

(Continued)

OTHER PUBLICATIONS

Communication Pursuant to Article 94(3) EPC Dated Apr. 25, 2023 From the European Patent Office Re. Application No. 21701165.9 (5 Pages).

(Continued)

*Primary Examiner* — Eric D. Bertram

(57) ABSTRACT

An implantable device containing a plurality of batteries, the plurality of batteries including at least one first non-rechargeable battery, and at least one second rechargeable battery. A method for providing power for a Cardiac Contractility Modulation Implantable Cardioverter Defibrillator (ICD) device, the method including providing power for cardioversion or defibrillation operation by a first, non-rechargeable battery, and providing power for Cardiac Contractility Modulation operation by a second, rechargeable battery. A method for controlling power for an implantable device having a rechargeable battery, a non-rechargeable battery and a Cardioverter Defibrillator module, the method including measuring electric power level of the rechargeable battery, comparing the rechargeable battery level to a threshold, if the electric power level of the rechargeable battery is less than the threshold, then providing power for the device from the non-rechargeable battery. Related apparatus and methods are also described.

13 Claims, 11 Drawing Sheets

(56) References Cited

U.S. PATENT DOCUMENTS

| | | | |
|---|---|---|---|
| 6,650,942 B2 * | 11/2003 | Howard | A61N 1/3754 |
| | | | 607/34 |
| 7,495,413 B2 * | 2/2009 | Vaisnys | A61N 1/3975 |
| | | | 320/103 |
| 8,676,310 B2 | 3/2014 | Burnes et al. | |
| 8,901,878 B2 | 12/2014 | Prutchi et al. | |
| 9,216,296 B2 | 12/2015 | Kameli | |
| 9,861,828 B2 | 1/2018 | Norton et al. | |
| 9,956,390 B2 | 5/2018 | Rousso et al. | |
| 11,547,863 B1 * | 1/2023 | Shaker | A61N 1/3904 |
| 11,794,026 B1 * | 10/2023 | Bardy | A61N 1/3981 |
| 2003/0080712 A1 * | 5/2003 | Tamura | A61N 1/3975 |
| | | | 320/103 |
| 2010/0114215 A1 | 5/2010 | Burnes et al. | |
| 2010/0191307 A1 | 7/2010 | Fang et al. | |
| 2011/0202101 A1 * | 8/2011 | Tan | G09B 19/003 |
| | | | 607/7 |
| 2012/0019115 A1 | 1/2012 | Dunwoody et al. | |
| 2014/0324111 A1 * | 10/2014 | Wu | A61N 1/3968 |
| | | | 607/7 |
| 2016/0067508 A1 | 3/2016 | Boone et al. | |
| 2018/0280708 A1 * | 10/2018 | Escalona | H02J 50/10 |
| 2019/0044362 A1 * | 2/2019 | Beyer | H02J 7/00714 |
| 2019/0356492 A1 * | 11/2019 | Picco | H04L 67/125 |
| 2021/0093877 A1 * | 4/2021 | Beyer | H02J 7/007182 |
| 2023/0041857 A1 * | 2/2023 | Prutchi | A61N 1/378 |
| 2023/0089192 A1 * | 3/2023 | Bennett | A61N 1/046 |
| | | | 607/142 |

FOREIGN PATENT DOCUMENTS

| | | |
|---|---|---|
| WO | WO 2016/039874 | 3/2016 |
| WO | WO 2021/137201 | 7/2021 |

OTHER PUBLICATIONS

International Preliminary Report on Patentability Dated Jul. 14, 2022 From the International Bureau of WIPO Re. Application No. PCT/IB2021/050031. (10 Pages).

International Search Report and the Written Opinion Dated Mar. 16, 2021 From the International Searching Authority Re. Application No. PCT/IB2021/050031. (14 Pages).

Translation Dated Sep. 12, 2022 of Notification of Office Action Dated Aug. 26, 2022 From the China National Intellectual Property Administration Re. Application No. 202180001559.4. (10 Pages).

Communication Pursuant to Article 94(3) EPC Dated Jan. 31, 2024 From the European Patent Office Re. Application No. 21701165.9 (7 Pages).

Communication Pursuant to Article 94(3) EPC Dated Jun. 29, 2023 From the European Patent Office Re. Application No. 21701165.9 (7 Pages).

Notification of Office Action and Search Report Dated Aug. 26, 2022 From the State Intellectual Property Office of the People's Republic of China Re. Application No. 202180001559.4. (9 Pages).

Notification of Office Action Dated Dec. 28, 2022 From the State Intellectual Property Office of the People's Republic of China Re. Application No. 202180001559.4 and Its English Summary. (6 Pages).

* cited by examiner

IMPLANTABLE CARDIOVERTER DEFIBRILLATOR (ICD) DEVICE WITH HIGH LONGEVITY

RELATED APPLICATION/S

This application is a National Phase of PCT Patent Application No. PCT/IB2021/050031 having International filing date of Jan. 5, 2021, which claims the benefit of priority under 35 USC § 119(e) of U.S. Provisional Patent Application No. 62/957,243, filed on Jan. 5, 2020.

The contents of the above applications are all incorporated by reference as if fully set forth herein in their entirety.

FIELD AND BACKGROUND OF THE INVENTION

The present invention, in some embodiments thereof, relates to an implantable cardiac device with a long power supply life, high longevity and, more particularly, but not exclusively to an Implantable Cardioverter Defibrillator (ICD) device with high longevity, and, yet more particularly, but not exclusively, to an implantable ICD which is a Cardioverter Defibrillator plus Cardiac Contractility Modulation device with high longevity.

An implantable cardioverter-defibrillator (ICD) is a device implantable inside the body, able to perform cardioversion and defibrillation. The ICD is a first-line treatment and prophylactic therapy for patients at risk for sudden cardiac death due to ventricular fibrillation and ventricular tachycardia. Current devices can be programmed to detect abnormal heart rhythms and deliver therapy via programmable anti-tachycardia pacing in addition to low-energy and high-energy shocks.

Cardiac contractility modulation treatment is delivered by a pacemaker-like device that applies Non-excitatory Electrical Signals (NES), adjusted to and synchronized with electrical action in a cardiac cycle. Other than a pacemaker, which delivers an electrical signal with an intention to result in cardiac contraction, the CARDIAC CONTRACTILITY MODULATION treatment applies the NES, adjusted to and synchronized with electrical action in the cardiac cycle.

Additional Background Art Includes:

U.S. Pat. No. 9,956,390 to Rousso et al.

The disclosures of all references mentioned above and throughout the present specification, as well as the disclosures of all references mentioned in those references, are hereby incorporated herein by reference.

SUMMARY OF THE INVENTION

The present invention, in some embodiments thereof, relates to an implantable cardiac device with two or more batteries, with at least two batteries having different attributes, suitable for different uses. In some embodiments, further relating to controlling power supply from the batteries for the various medical uses.

According to an aspect of some embodiments of the present invention there is provided an implantable device containing a plurality of batteries, the plurality of batteries including at least one first non-rechargeable battery, and at least one second rechargeable battery.

According to some embodiments of the invention, the implantable device is comprised within a single housing.

According to some embodiments of the invention, the implantable device is configured so that either the first non-rechargeable battery or the second rechargeable battery may power a same output lead.

According to some embodiments of the invention, the implantable device is an Implantable Cardioversion Device (ICD).

According to some embodiments of the invention, the first non-rechargeable battery and the second rechargeable battery are attached to a same circuit board.

According to some embodiments of the invention, the first non-rechargeable battery is configured to deliver cardiac defibrillation shock powered by the first non-rechargeable battery.

According to some embodiments of the invention, the second rechargeable battery is configured to deliver Cardiac Contractility Modulation therapy powered by the second rechargeable battery. According to some embodiments of the invention, the second rechargeable battery is configured to deliver cardiac pacing powered by the second rechargeable battery.

According to some embodiments of the invention, further including a processor for measuring electric signals and controlling supplying power for an electric circuit between the first non-rechargeable battery and the second rechargeable battery.

According to some embodiments of the invention, the processor is configured to measure a patient's vital signs. According to some embodiments of the invention, the processor is configured to measure a patient's physiological parameter.

According to some embodiments of the invention, the processor is configured to use electric power from the second rechargeable battery.

According to some embodiments of the invention, the first non-rechargeable battery is an ICD battery.

According to some embodiments of the invention, further including a controller for switching supplying power for an electric circuit between the first non-rechargeable battery and the second rechargeable battery.

According to some embodiments of the invention, the first non-rechargeable battery is a high current battery and the second rechargeable battery is a low current battery.

According to some embodiments of the invention, the device is arranged so the first, non-rechargeable, battery provides power for cardioversion or defibrillation to a cardioversion or a defibrillation lead.

According to some embodiments of the invention, the device is arranged so the first, non-rechargeable, battery provides power to for treating a defibrillation event.

According to some embodiments of the invention, the device is arranged so the first, non-rechargeable, battery provides power to charge a capacitor for treating a defibrillation event using the first, non-rechargeable, battery.

According to some embodiments of the invention, the device is arranged for providing power to a Cardiac Contractility Modulation lead using the second, rechargeable, battery.

According to some embodiments of the invention, further including a micro-controller arranged for sensing when the second, rechargeable battery cannot provide power for an operation powered by the second battery and providing power from the first, non-rechargeable battery for the operation.

According to an aspect of some embodiments of the present invention there is provided a method for providing power for a Cardiac Contractility Modulation Implantable Cardioverter Defibrillator ICD device, the method including providing power for cardioversion or defibrillation operation by a first, non-rechargeable battery, and providing power for Cardiac Contractility Modulation operation by a second, rechargeable battery.

According to some embodiments of the invention, further including using a micro-controller for sensing when the second, rechargeable battery cannot provide power for an operation powered by the second, rechargeable battery and providing power from the first, non-rechargeable battery for the operation.

According to some embodiments of the invention, the second, rechargeable battery is a rechargeable battery.

According to an aspect of some embodiments of the present invention there is provided a method for controlling power for an implantable device having a rechargeable battery, a non-rechargeable battery and a Cardioverter Defibrillator module, the method including measuring electric power level of the rechargeable battery, comparing the rechargeable battery level to a threshold, if the electric power level of the rechargeable battery is less than the threshold, then providing power for the device from the non-rechargeable battery.

According to an aspect of some embodiments of the present invention there is provided a method for controlling power for an implantable device having a rechargeable battery, a non-rechargeable battery an Implantable Cardioverter Defibrillator (ICD) unit and a Cardiac Contractility Modulation unit, the method including comparing a rechargeable battery level to a first threshold, if the electric power level of the rechargeable battery is less than the first threshold, then sustaining ICD module operation using electric current from the rechargeable battery and not sustaining Cardiac Contractility Modulation operation, and comparing the rechargeable battery level to a second threshold, wherein if the electric power level of the rechargeable battery is less than the second threshold then sustaining the ICD module operation includes using electric current from the non-rechargeable battery.

According to some embodiments of the invention, if the electric power level of the rechargeable battery is less than the first threshold then setting an alert to recharge the rechargeable battery.

According to some embodiments of the invention, the first threshold is at a higher level than the second threshold.

According to some embodiments of the invention, the first threshold is equal to the second threshold.

According to an aspect of some embodiments of the present invention there is provided a method for controlling power for an implantable device having a rechargeable battery, a non-rechargeable battery and a Cardioverter Defibrillator module, the method including measuring an electric power level of the rechargeable battery, comparing the rechargeable battery level to a first threshold, if the electric power level of the rechargeable battery is less than the first threshold then comparing the rechargeable battery level to a second threshold, wherein if the electric power level of the rechargeable battery is less than the second threshold, then switching providing power from the rechargeable battery to the non-rechargeable battery.

According to some embodiments of the invention, if the electric power level of the rechargeable battery is less than the first threshold then setting an alert to recharge the rechargeable battery.

According to some embodiments of the invention, the first threshold is at a higher level than the second threshold.

According to some embodiments of the invention, the first threshold is equal to the second threshold.

According to an aspect of some embodiments of the present invention there is provided a method for controlling power for an implantable device having a rechargeable battery, a non-rechargeable battery a Cardioverter Defibrillator module and a Cardiac Contractility Modulation stimulation module, the method including measuring an electric power level of the rechargeable battery, comparing the level of the rechargeable battery to a first threshold, if the electric power level of the rechargeable battery is less than the threshold then stopping Cardiac Contractility Modulation stimulation, and using energy from the rechargeable battery for Cardioverter Defibrillator sensing and housekeeping, and comparing the level of the rechargeable battery to a second threshold, wherein if the electric power level of the rechargeable battery is less than the second threshold, then providing power for Cardioverter Defibrillator operation from the non-rechargeable battery.

According to some embodiments of the invention, if the electric power level of the rechargeable battery is less than a third threshold then setting an alert to recharge the rechargeable battery.

According to some embodiments of the invention, the third threshold is at a higher level than the first threshold.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as switching power supply between batteries of different types in an implantable device, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWING(S)

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

Figure 7:
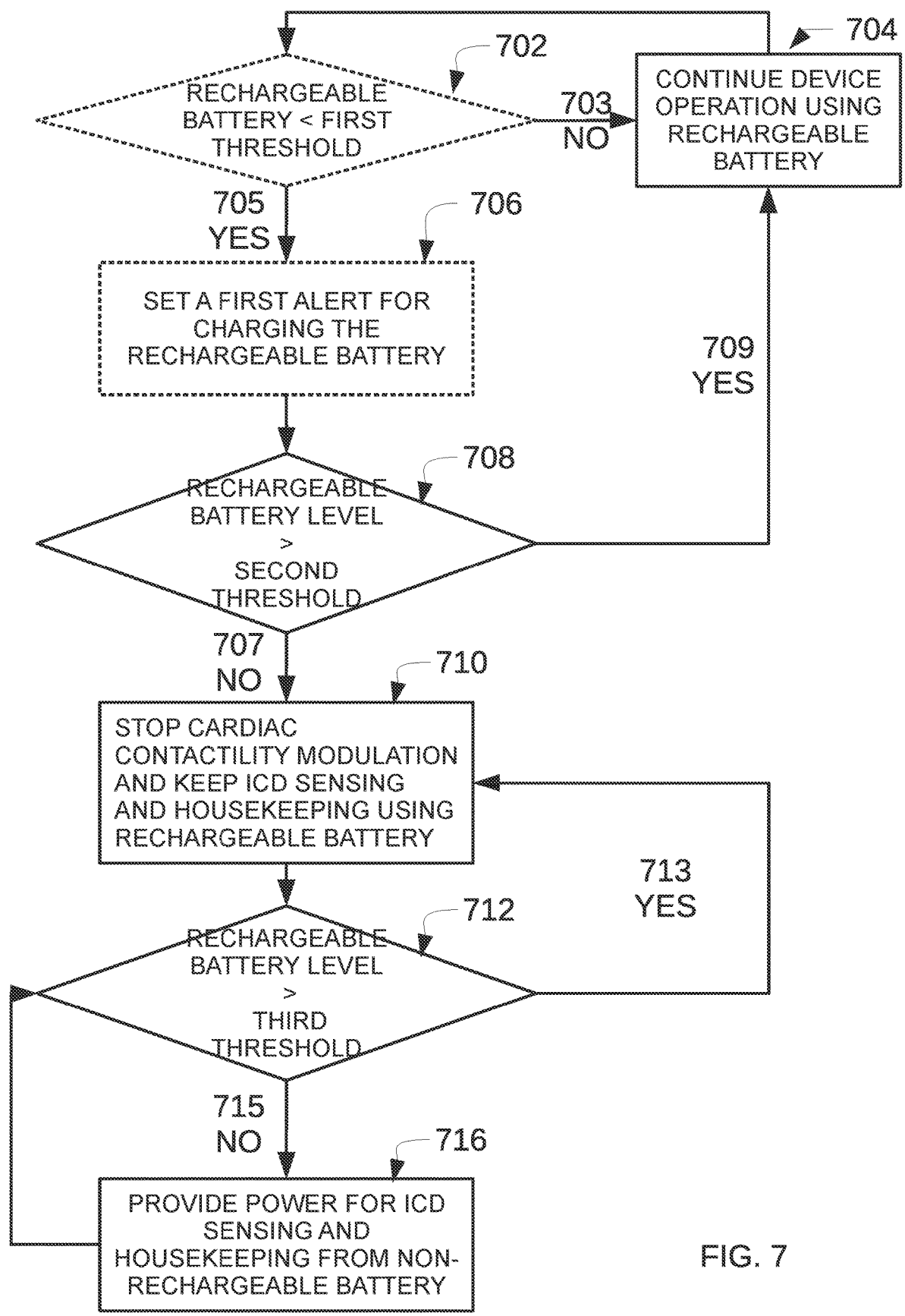
Figure 8:
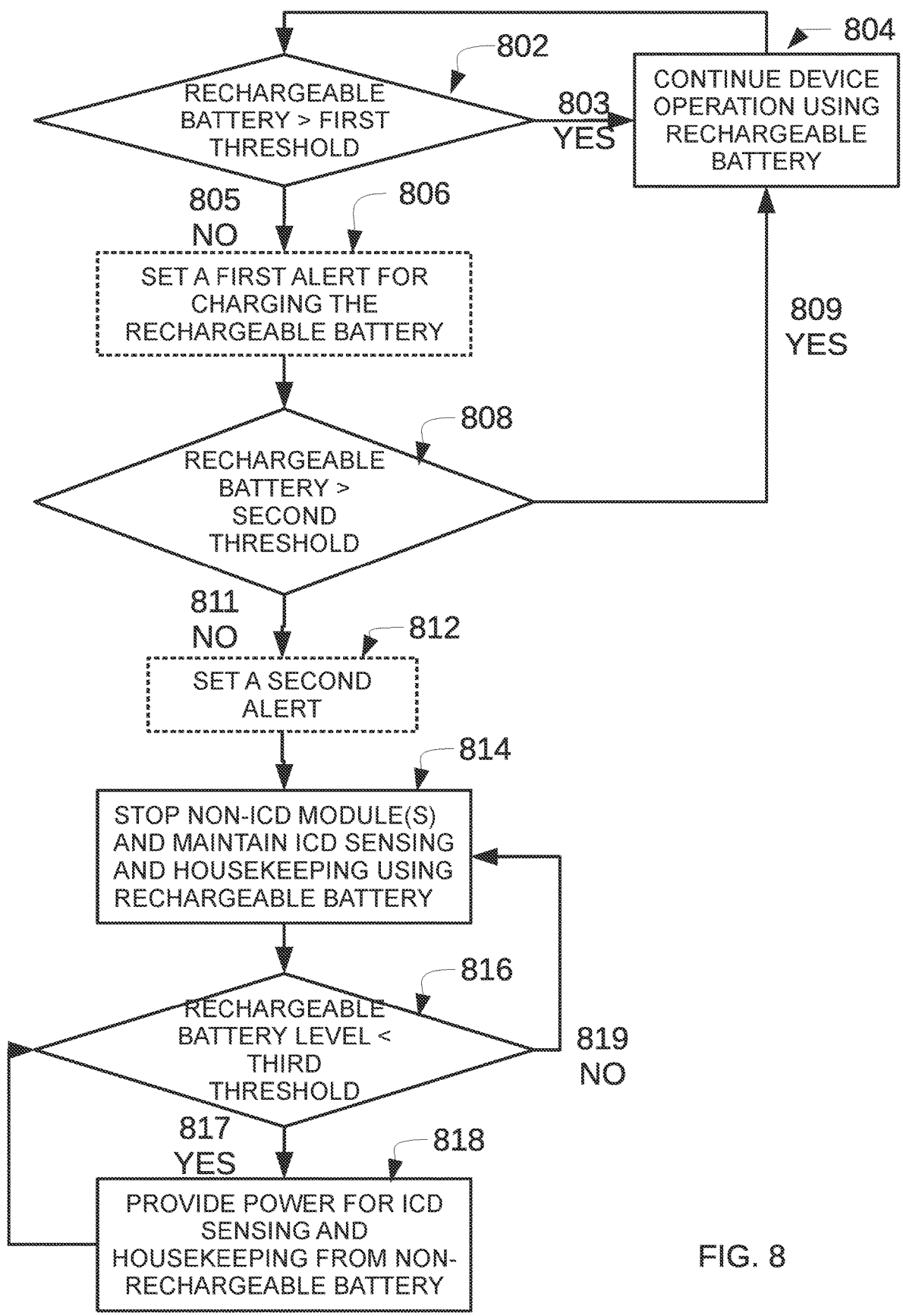

FIG. 7 is a simplified flow chart illustration of a method for controlling power for an ICD (Cardiac Contractility Modulation plus Implantable Cardioverter Defibrillator) device according to an example embodiment of the invention; and FIG. 8 is a simplified flow chart illustration of a method for controlling power for an ICD plus a sensing and/or monitoring configuration according to an example embodiment of the invention.

DESCRIPTION OF SPECIFIC EMBODIMENTS OF THE INVENTION

The present invention, in some embodiments thereof, relates to an implantable cardiac device with a long power supply life, high longevity and, more particularly, but not exclusively to a Cardiac Contractility Modulation device with high longevity, and, yet more particularly, but not exclusively, to an implantable Cardioverter Defibrillator plus Cardiac Contractility Modulation device with high longevity.

Definitions

The term "cell" in all its grammatical forms is used in the present application and claims to describe an electric power source of all types, the source including a chemical cell, a rechargeable cell, a non-rechargeable cell, a primary cell, a secondary cell, and even a capacitor and/or a super capacitor and/or an ultra-capacitor.

The terms "cell" and "battery" in all their grammatical forms are used interchangeably in the present application and claims to describe an electric power source which includes one or more cells.

The terms "primary cell" and "primary battery" in all their grammatical forms are used in the present application and claims to describe a single-use, or typically non-rechargeable. A common example of a primary cell can be an alkaline battery, a Li-SVO (Lithium/Silver Vanadium Oxide) and a hybrid Li-CFx/SVO (Lithium/Carbon monoFluoride Silver Vanadium Oxide).

The terms "secondary cell" and "secondary battery" in all their grammatical forms are used in the present application and claims to describe a rechargeable cell or battery. A common example can be a Lithium-ion battery.

The term "high current" battery in all its grammatical forms is used in the present application and claims to describe a battery capable of a relatively higher rate of discharge, that is, higher current, than a battery described as a "low current" battery in all its grammatical forms.

A low current battery as described herein generally provides current in a range of 10-250 milli-amperes (mA), typically 100 mA.

A high current battery as described herein generally provides current in a range of 1-10 Amperes (A), typically 6 mA.

Various attributes of batteries include electric capacity, internal resistance, voltage, current intensity which a battery is optimized to provide, time a battery can hold a charge, and additional features which persons skilled in the art use when designing battery powered systems.

Overview

Implanted medical devices which use a battery for providing electric power are known.

In practice, there are implantable-grade rechargeable batteries, for example Lithium-ion batteries, usually capable of delivering relatively small currents, for example a maximum of 100 mA, and there are also implantable-grade batteries capable of higher-current operation, for example Li-SVO (Lithium/Silver Vanadium Oxide) and hybrid Li-CFx/SVO (Lithium/Carbon monoFluoride Silver Vanadium Oxide).

Various uses of electric power sometimes call for various batteries.

By way of a non-limiting example, in implantable cardiac devices such as an Implantable Cardioverter Defibrillator (ICD), there are some uses with low current demand (e.g. Cardiac Contractility Modulation therapy, sensing, VT/VF (Ventricular Tachycardia/Ventricular Fibrillation) detection, housekeeping, communications, operation of non-electric-shock components in the implantable device, etc.), and some uses with significantly higher current demand (e.g. cardioversion and/or defibrillation).

The term "housekeeping" is used in the present specification and claims to mean routine checks of the device integrity, functioning and operation.

An aspect of some embodiments of the invention relates to providing two batteries in an implantable device.

Having different batteries with different attributes can potentially provide an improved implantable device. Some fields of potential improvement include one or more of:

- a longer device life, optionally based on lowering use of a non-rechargeable battery, where routine power consumption is optionally provided from a rechargeable battery;
- the batteries can optionally back each other up, so that when one battery cannot supply power, another battery may optionally supply the power;
- a higher current battery can be included, potentially providing a higher maximum current, while optionally simultaneously operating low-power operation from a lower current battery; and
- a higher current battery can be included, potentially providing several levels of high current operations, while optionally having a battery optimized for low current operation for low current operations.

In some embodiments, two batteries are included in an implantable device, one battery for low current operations and one battery for high current operations.

In some embodiments, more than two batteries are included.

Some potential advantages of using two batteries are included in an implantable device, one battery for low current operations and one battery for high current operations include:

Using a rechargeable battery for low current uses such as Cardiac Contractility Modulation therapy, sensing, VT/VF detection, housekeeping, communications, can potentially keep more electric energy stored in a non-rechargeable battery for uses which draw higher current, such cardioversion and/or defibrillation.

Having a non-rechargeable battery in an implantable device potentially provides backup electric power for low current uses such as Cardiac Contractility Modulation therapy, sensing, VT/VF detection, housekeeping, communications, if a rechargeable battery charge level is below a specific threshold. In some embodiments when a controller detects that the rechargeable battery is below the specific threshold the controller switches providing electric power to some or all the low current uses from the non-rechargeable battery. In some embodiments when a controller detects that the rechargeable battery is back above the specific threshold, for example by the rechargeable battery having been recharged, the controller switches providing electric power to some or all the low current back to the rechargeable battery.

When describing two or more batteries, it is noted that in some embodiments the batteries may have the same attributes, and in some embodiments the batteries may have different attributes.

Strategies for Smart Use of Multiple Batteries.

An aspect of some embodiments of the invention relates to managing the use of multiple batteries.

Some non-limiting examples of managing multiple batteries are described below, using language referring to a non-limiting example of one non-rechargeable battery and one rechargeable battery.

In some embodiments, power for low current functions is provided only by a rechargeable battery, and when the rechargeable battery charge reaches a threshold, changes are optionally made to management of the low current functions. Some non-limiting examples of such management changes include:

performing the low current functions at a lower frequency, so as to conserve power in the rechargeable battery;

skipping some low current functions and/or performing the low current functions at a lower frequency, optionally dynamically based on a level of remaining power so as to conserve power in the rechargeable battery; and skipping some low current functions and/or performing the low current functions at a lower frequency, optionally based on maintaining some medically more-important functions and sacrificing some medically less important function by skipping some of the less important functions and/or performing the less important functions at a lower frequency so as to conserve power in the rechargeable battery.

It is noted that when the rechargeable battery is recharged, functions which were sacrificed are optionally restarted. The methods described herein for gradual sacrificing of functions based on gradual reduction of battery power are optionally used in the opposite direction, by restarting functions based on gradual increase of battery power.

In some embodiments, the method for managing which function is powered by which battery is optionally a static method, that is, specific functions are powered by a specific battery, and when that battery does not have enough power, the functions of that battery are not performed.

In some embodiments, the method for managing which function is powered by which battery is optionally a dynamic method, that is, specific functions are initially powered by a specific battery, and when that battery does not have enough power, some or all of the functions of that battery may optionally be transferred to another battery. by way of a non-limiting example some sensing functions, typically powered by a rechargeable battery, may be provided power from a non-rechargeable battery, for example sensing and/monitoring a patient's need for shock therapy may be provided power from a non-rechargeable battery so that such shock therapy can be initiated when needed.

In some embodiments, a non-rechargeable battery is kept disconnected from the implantable device until its power is determined to be needed. Such disconnection potentially extends the non-rechargeable battery charge.

By way of a non-limiting example, the following table describes gradual progression of reducing electric power use from a rechargeable battery for various implantable device functions:

TABLE 1

| Function | Threshold 1 | Threshold 2 |
| --- | --- | --- |
| Non-life-saving | Provide alert | Stop non-life-saving functions |
| Life-saving | Provide alert | Use non-rechargeable battery |

Some non-limiting example embodiments of life-saving functions which are relevant to the above table include: cardioversion, defibrillation in case of VF and/or VT, pacing in patients that have AV block and/or AV ablation, pacing in patients that have sick sinus syndrome. In some embodiments VF and/or VT are detected by the device. In some embodiments AV block and/or AV ablation are conditions which are known in advance of implanting the device, and optionally set as a known parameter for managing battery use in the implantable device.

Some non-limiting example embodiments of non-life-saving functions which are relevant to the above table include: housekeeping (as described elsewhere herein), Cardiac Contractility Modulation, CRT, bio impedance sensing and blood pressure sensing.

Battery Types

Some non-limiting example types of batteries include:

a high discharge rate battery, also termed herein a high current battery;

a low discharge rate battery, also termed herein a low current battery;

a rechargeable battery;

a non-rechargeable battery;

a capacitor; and a super capacitor.

Some typical battery specifications:

Rechargeable battery:

Typical capacity—100-300 mAh; and

Typical max current—100 mA.

Non-rechargeable, also termed primary, ICD battery:

Typical capacity—2000 mAh; and

Typical max current—6 A.

Example Uses

Example uses of electric power in an implantable cardiac device include:

Cardiac Contractility Modulation therapy;

sensing medical signals;

Ventricular Tachycardia (VT) detection;

Ventricular Fibrillation (VF) detection;

Pacing;

Anti-Tachycardia Pacing (ATP);

housekeeping, such as monitoring remaining battery capacity, charging capacitors, controlling/connecting electric power sources to leads for medical operations;

communications, such as within the implantable device and/or to devices outside of the implantable device;

cardioversion;

cardioverter functions;

defibrillator functions;

pacemaker functions; and implantable monitoring functions that may include pressure sensing, ECG sensing, bio-impedance sensing, accelerometer sensing and position sensing.

Cardioversion and Defibrillation.

Cardioversion is a delivery of energy which is synchronized to the cardiac QRS complex.

Defibrillation is a non-synchronized delivery of a shock during the cardiac cycle.

In an implantable device, one or both of cardioversion and defibrillation are typically used to provide electrical shock during ventricle tachycardia or ventricle fibrillation.

A typical energy for ICD shock is in a range of 30-45 Joules. This value is higher for a subcutaneous ICD, reaching 70 Joules.

In some cases, the level of energy is determined by testing: During ICD implantation, a Defibrillation Threshold Test (DFT) is carried out by Ventricle Fibrillation (VF) induction and shock therapy from the implanted device, evaluating the necessary energy for an effective defibrillation. Normally, a margin of safety considered adequate is 10 Joules above a measured value of the DFT.

Example Categories of Operation Types in an ICD

Some non-limiting example categories of operation types in an ICD include:
- immediate need—an operation to be performed as soon as possible, may include defibrillation, pacing, cardioversion, when such is determined to be needed, optionally by a computing unit within the ICD, to be immediately needed;
- short-term need—an operation to be performed soon, by way of a non-limiting example within a few seconds (for example 1, 5, 10, 20, 30, 40, 50, 60 seconds), a minute, or a few minutes. Such an operation may include defibrillation, pacing, cardioversion, when such is determined to be needed, optionally by a computing unit within the ICD. A short-term need operation may allow a choice between, for example, using a high current battery or charging a capacitor by a low current battery;
- long-term need—an operation to be performed eventually, by way of a non-limiting example within a few seconds, a minute, a few minutes, a few hours, yet can be postponed to save battery life, for example by scheduling the operation for after recharging a rechargeable battery. A non-limiting example of such a long-term need operation may be a life quality improvement operation (see below) such as Cardiac Contractility Modulation;
- life-saving operations, such as, by way of a non-limiting example, when an immediate need is determined for intervening with a cardiac rhythm, lest a patient die. In some embodiments a life-saving operation may optionally use electric power from a non-rechargeable battery. In some embodiments a life-saving operation may optionally use electric power from whatever battery can be used;
- life quality improvement operations, such as, by way of a non-limiting example, Cardiac Contractility Modulation for a patient with an impaired but not life threatening cardiac rhythm. In some embodiments a life-saving operation may optionally use electric power from a rechargeable battery, saving power stored in a non-rechargeable battery; and
- housekeeping operations, such as by way of a non-limiting example, communications with external devices.

Typical Uses of Battery Types

In some embodiments, and not necessarily all embodiments, a rechargeable battery is typically used for electrical sensing, for example sensing for implantable devices like ICD, pacemaker, CRT and Cardiac Contractility Modulation, and/or for delivering pacing or stimulation energy needed for cardiac pacing and Cardiac Contractility Modulation stimulation, and/or computing in an implantable device, and/or decision making in an implantable device.

In some embodiments, a non-rechargeable battery is typically used for performing Cardioversion or defibrillation.

Optional Simultaneous Use of Battery Types

In some embodiments, two different types of battery are optionally used simultaneously for a same operation.

In some embodiments, two different types of battery are optionally used simultaneously for different operations.

In some embodiments, two different types of battery are optionally used simultaneously when a first rechargeable battery does not have enough energy for a needed operation and a second non-rechargeable battery is used to provide the additional energy needed.

Controlling Electric Power

In some embodiments, if a capacitor is charged for defibrillation and/or cardioversion, and sensing determines that the defibrillation and/or cardioversion are not needed any more, at least some of the electric charge in the capacitor is optionally used for recharging a rechargeable battery.

In some embodiments, Cardiac Contractility Modulation operation is optionally stopped in order to keep enough energy in a rechargeable battery for one shock cycle and/or for 1-7 days of pacing.

In some embodiments, energy deflation of a first permanent battery is optionally reduced by keeping an electrical potential difference between the first battery poles at a specific value by using power from second rechargeable battery.

A Three-Battery Configuration

In some embodiments, three batteries are optionally used, for example a rechargeable battery, optionally a low current battery; a non-rechargeable battery, optionally a high current non-rechargeable battery; and a capacitor or super capacitor.

Additional Discussion of Some Non-Limiting Example Embodiments

A non-limiting example embodiment of the invention includes a combined Cardiac Contractility Modulation and ICD implantable device that incorporates a first rechargeable battery and a second non-rechargeable battery. In the device, as long as a patient is compliant with recharging instructions, power for one or more of Cardiac Contractility Modulation therapy, sensing, VT/VF detection, pacing and housekeeping operations is optionally provided by the first rechargeable battery, and the second battery is optionally disconnected, potentially maximizing the second battery's availability when needed.

In practice, first type implantable-grade rechargeable batteries (e.g. Lithium-ion) are typically capable of delivering relatively small currents (e.g. 100 mA maximum), while there are second type small, implantable-grade batteries capable of high current operation (e.g. Li-SVO or hybrid Li-CFx/SVO). As such, as long as there is enough charge in the first type rechargeable battery, operations with low current demand (e.g. Cardiac Contractility Modulation therapy, sensing, VT/VF detection, pacing, housekeeping, communications, etc.) are optionally powered from the first type rechargeable battery.

When cardioversion or defibrillation is required, energy is optionally taken from the second type high current non-rechargeable battery.

When insufficient charge is left in the first type rechargeable battery due to non-compliance or battery depletion, power for the life-support operations (including those which have low current demand such as sensing, pacing, VT/VF detection, etc.) is optionally taken from the second type non-rechargeable battery.

A setup as described above potentially maximizes longevity of the implantable device by making use of the second type non-rechargeable battery to a minimum without placing the patient in danger when the first type rechargeable battery becomes discharged.

In some embodiments, an ICD module is designed to be powered from two implantable-grade batteries:

1. A commercially-available, implantable-grade, 200-220 mAh Li-ion rechargeable battery. An example battery can be the Quallion QL0200I-A or the Greatbatch 2993.

2. A commercially-available, implantable-grade, high current Lithium non-rechargeable and/or primary battery (e.g. Li-SVO or hybrid Li-CFx/SVO). An example battery can be the Greatbatch M3340 QHR battery.

During normal operation of the device, when the Li-ion battery has sufficient charge to power sensing, VT/VF detection and housekeeping operations, the ICD Module optionally derives power from the rechargeable battery to allow minimum use of the high current battery's charge.

Energy for ATP, defibrillation, induction, cardioversion, and post-shock Brady pacing is optionally derived from a high current non-rechargeable battery.

In some embodiments when the Li-ion battery does not have sufficient charge to power sensing, then the ICD Module optionally derives power for sensing, VT/VF detection and ICD-specific housekeeping operations from the high current Lithium non-rechargeable battery.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1A:
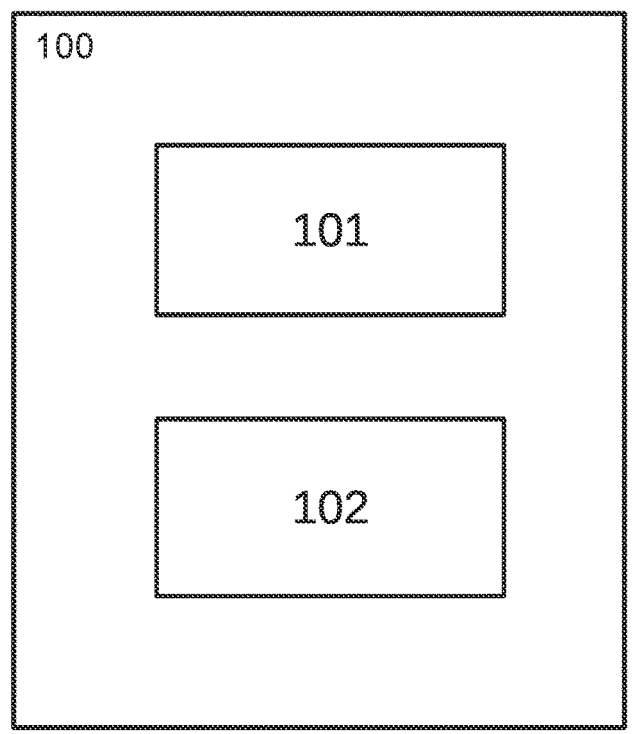
FIGS. 1A-1F are simplified illustrations of example embodiments of the invention.

Reference is now made to FIG. 1A, which is a simplified illustration of an example embodiment of the invention.

FIG. 1A shows an implantable device housing 100 containing two batteries 101 102. FIG. 1A is intended to illustrate that more than one battery 101 102 may be included in an implantable device housing 100.

In some embodiments, the batteries 101 102 are optionally attached to a same circuit board.

Figure 1B:
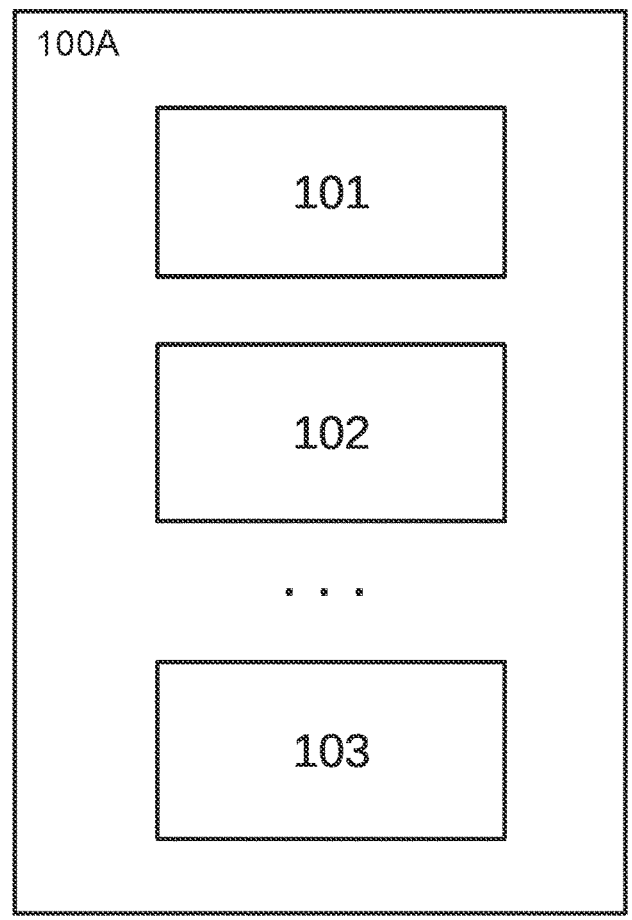

Reference is now made to FIG. 1B, which is a simplified illustration of an example embodiment of the invention.

FIG. 1B shows an implantable device housing 100A containing three batteries 101 102 103. FIG. 1B is intended to illustrate that more than two batteries may be included in an implantable device housing 100A, for example three batteries 101 102 103, and even more.

In some embodiments, the batteries 101 102 103, and optionally even more, are optionally attached to a same circuit board.

Further example embodiments will be described with reference to two batteries, with an intention that persons skilled in the art will understand how to implement similar embodiments with more than two batteries.

Figure 1C:
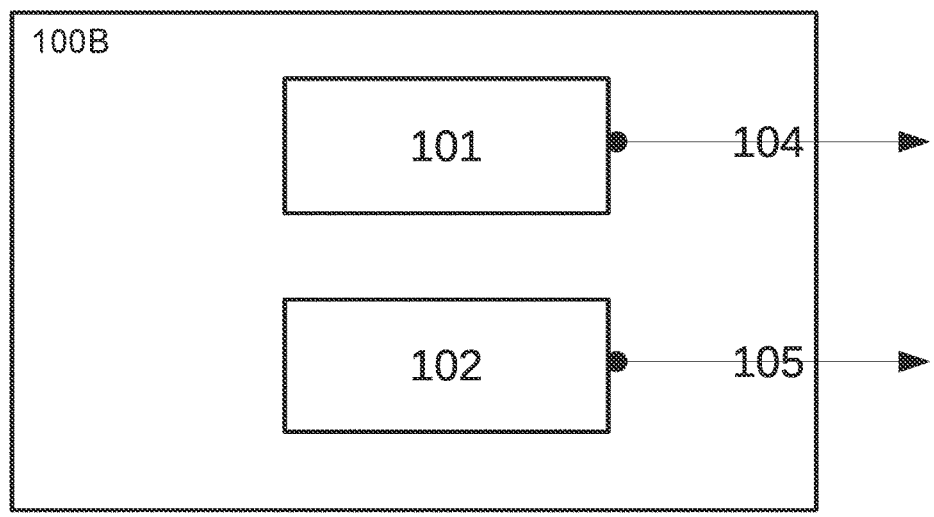

Reference is now made to FIG. 1C, which is a simplified illustration of an example embodiment of the invention.

FIG. 1C shows an implantable device housing 100B containing two batteries 101 102, each one of the batteries optionally powering a different output lead 104 105.

The term lead is used in the present application and claims to describe an electric conductor and/or electrode.

In some embodiments, a first battery 101 optionally provides power to a first output lead 104, for operations requiring electric power for which the first battery 101 is designed.

In some embodiments, a second battery 102 optionally provides power to a second output lead 105, for operations requiring electric power for which the second battery 102 is designed.

FIG. 1C is intended to illustrate that the two batteries 101 102 may be powering two different leads 104 105 in parallel.

In some embodiments, the batteries 101 102 are optionally attached to a same circuit board.

Figure 1D:
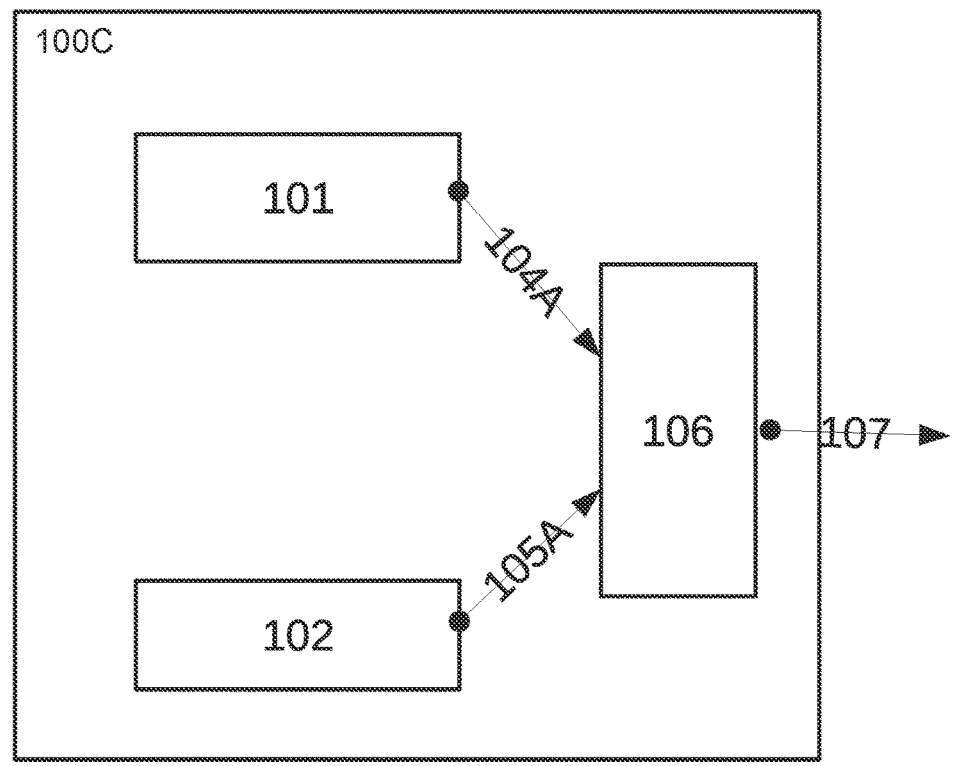

Reference is now made to FIG. 1D, which is a simplified illustration of an example embodiment of the invention.

FIG. 1D shows an implantable device housing 100C containing two batteries 101 102, each one of the batteries optionally supplying power 104A 105A to a controller 106, which optionally controls power output to an output lead 107.

FIG. 1D is intended to illustrate that the two batteries 101 102 may be powering a single output lead 107.

In some embodiments the controller 106 optionally provides power from a selected one of the two batteries 101 102 to the output lead 107 according to an operation which the controller optionally selects to perform.

In some embodiments the controller 106 optionally provides power from both of the two batteries 101 102 to the output lead 107 according to an operation which the controller optionally selects to perform.

In some embodiments the controller 106 optionally provides power from a not-depleted battery to the output lead 107 when one of the batteries 101 102 is sensed to be depleted.

In some embodiments, the controller 106 optionally provides power from a higher current battery, for example battery 102, to the output lead 107 when a lower current battery, for example battery 101, is sensed to be depleted.

In some embodiments operation of the controller 106 itself is optionally powered by a lower-current battery, for example battery 101.

In some embodiments, the batteries 101 102 are optionally attached to a same circuit board.

Figure 1E:
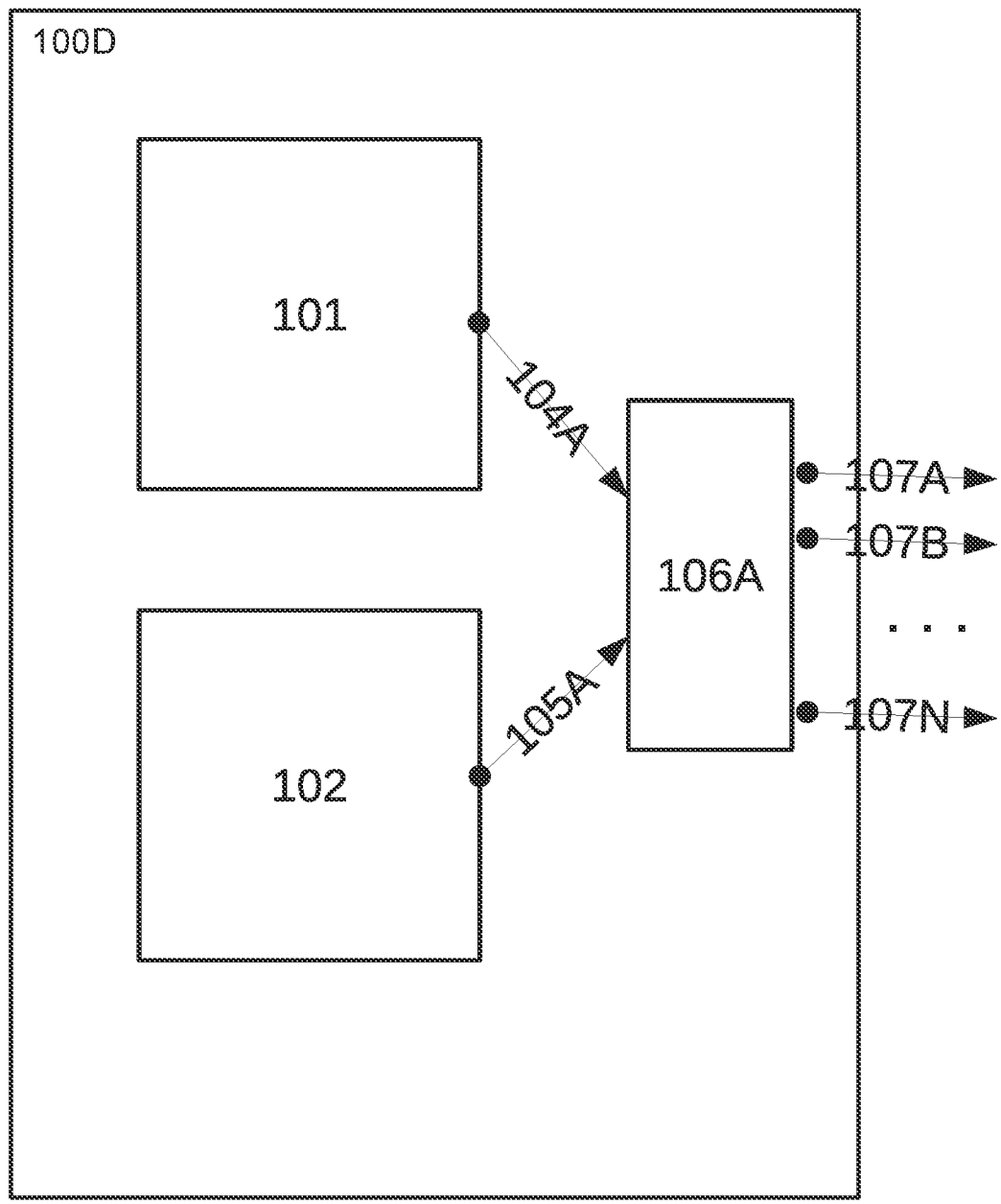

Reference is now made to FIG. 1E, which is a simplified illustration of an example embodiment of the invention.

FIG. 1E shows an implantable device housing 100D containing two batteries 101 102, each one of the batteries optionally supplying power 104A 105A to a controller 106A, which optionally controls power output to more than one output lead 107A 107B . . . 107N.

FIG. 1E is intended to illustrate that the two batteries 101 102 may be powering more than one output lead 107A 107B . . . 107N.

In some embodiments, a first battery 101 optionally supplies power 104A to the controller 106A, which optionally provides power to a first output lead 107A, optionally for operations requiring electric power for which the first battery 101 is designed.

In some embodiments, a second battery 102 optionally supplies power 105A to the controller 106A, which optionally provides power to a second output lead 107B, optionally for operations requiring electric power for which the second battery 102 is designed.

In some embodiments the controller 106A optionally provides power from a selected one of the two batteries 101 102 to a selected one of the output leads 107A 107B ... 107N according to an operation which the controller optionally selects to perform via the selected one of the output leads 107A 107B ... 107N.

In some embodiments, the batteries 101 102 are optionally attached to a same circuit board.

Figure 1F:
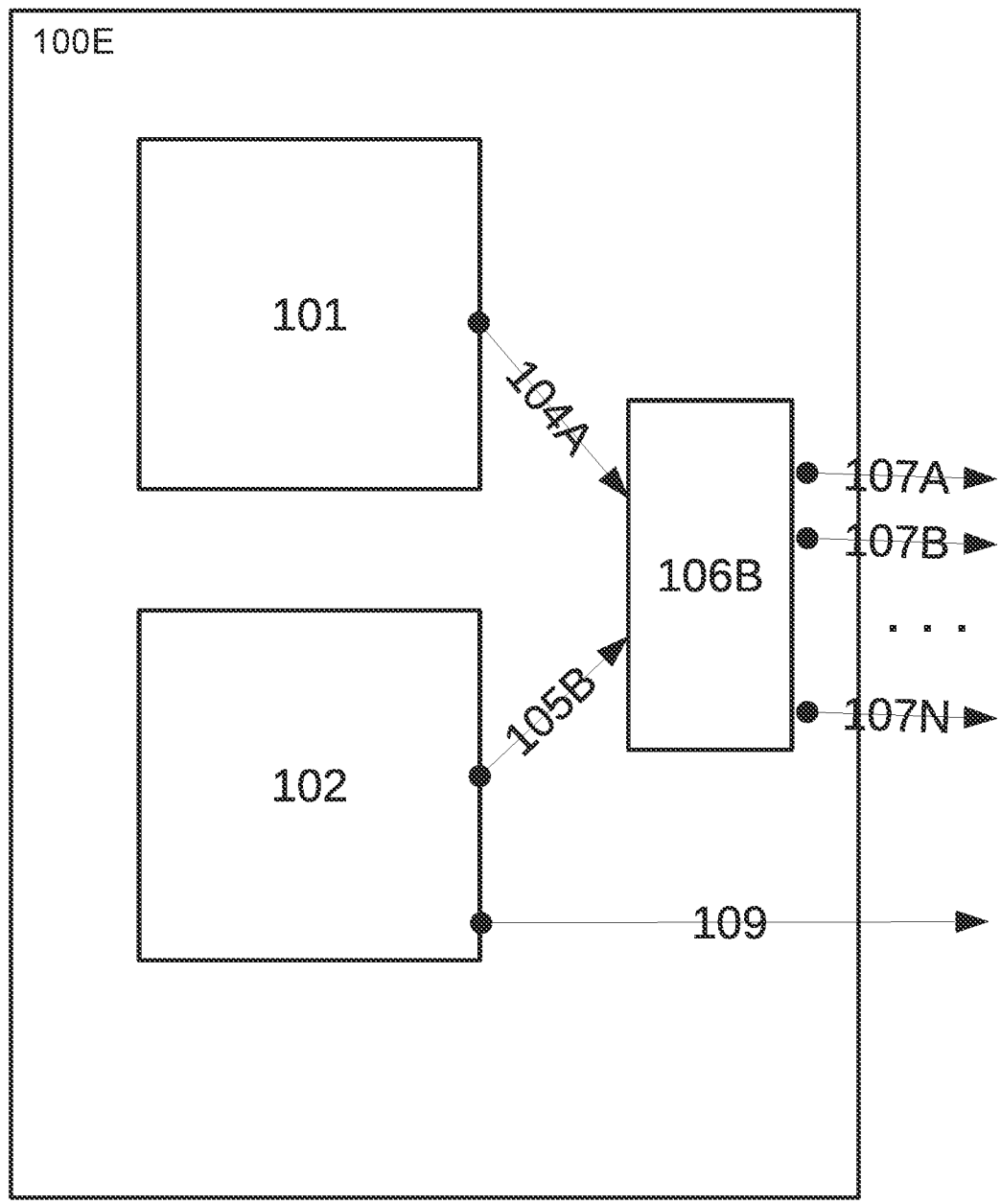

Reference is now made to FIG. 1F, which is a simplified illustration of an example embodiment of the invention.

FIG. 1F shows an implantable device housing 100E containing two batteries 101 102, each one of the batteries optionally supplying power 104A 105A to a controller 106B, which optionally controls power output to more than one output lead 107A 107B ... 107N, and one of the batteries 102 providing power output to a specific output lead 109.

FIG. 1F is intended to illustrate that one 102 of the two batteries 101 102 may be providing power 105B to a controller 106B, optionally acting as a backup battery 102 for operations controlled by the controller 106B.

In some embodiments a first battery 101 optionally supplies power 104A to the controller 106B, which optionally provides power to one or more selected output leads 107A 107B ... 107N, optionally for operations requiring electric power for which the first battery 101 is designed.

In some embodiments a second battery 102 optionally supplies power 105B to the controller 106B when need be. In some embodiments, the second battery 102 optionally supplies power 105B to the controller 106B when the first battery 101 cannot supply such power.

In some embodiments, the controller 106B is optionally designed to draw power from the second battery 102 only when the first battery 101 cannot supply such power.

In some embodiments, the second battery 102 optionally supplies power 105B to the controller 106B in parallel to providing power to the output lead 109.

In some embodiments, the second battery 102 is a non-rechargeable battery.

In some embodiments, the second battery 102 is arranged for providing power for cardioversion or defibrillation to a cardioversion or defibrillation lead.

In some embodiments, the output lead 109 is a cardioversion or defibrillation lead.

In some embodiments, the batteries 101 102 are optionally attached to a same circuit board.

Figure 2:
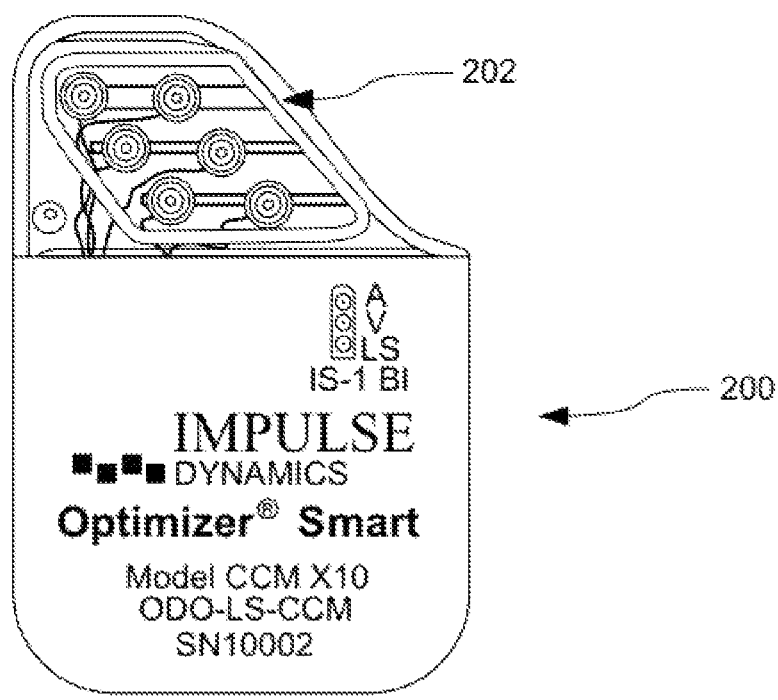
FIG. 2 is an image of an example embodiment of the invention.

Reference is now made to FIG. 2, which is an image of an example embodiment of the invention.

FIG. 2 shows a non-limiting example of an implantable device 200. The non-limiting example of the implantable device 200 shown in FIG. 2 is an Impulse Dynamics Cardiac Contractility Modulation device.

In some embodiments the device 200 may optionally contain two rechargeable batteries (not visible in FIG. 2) and a loop 202 used for recharging the device 200.

Figure 3:
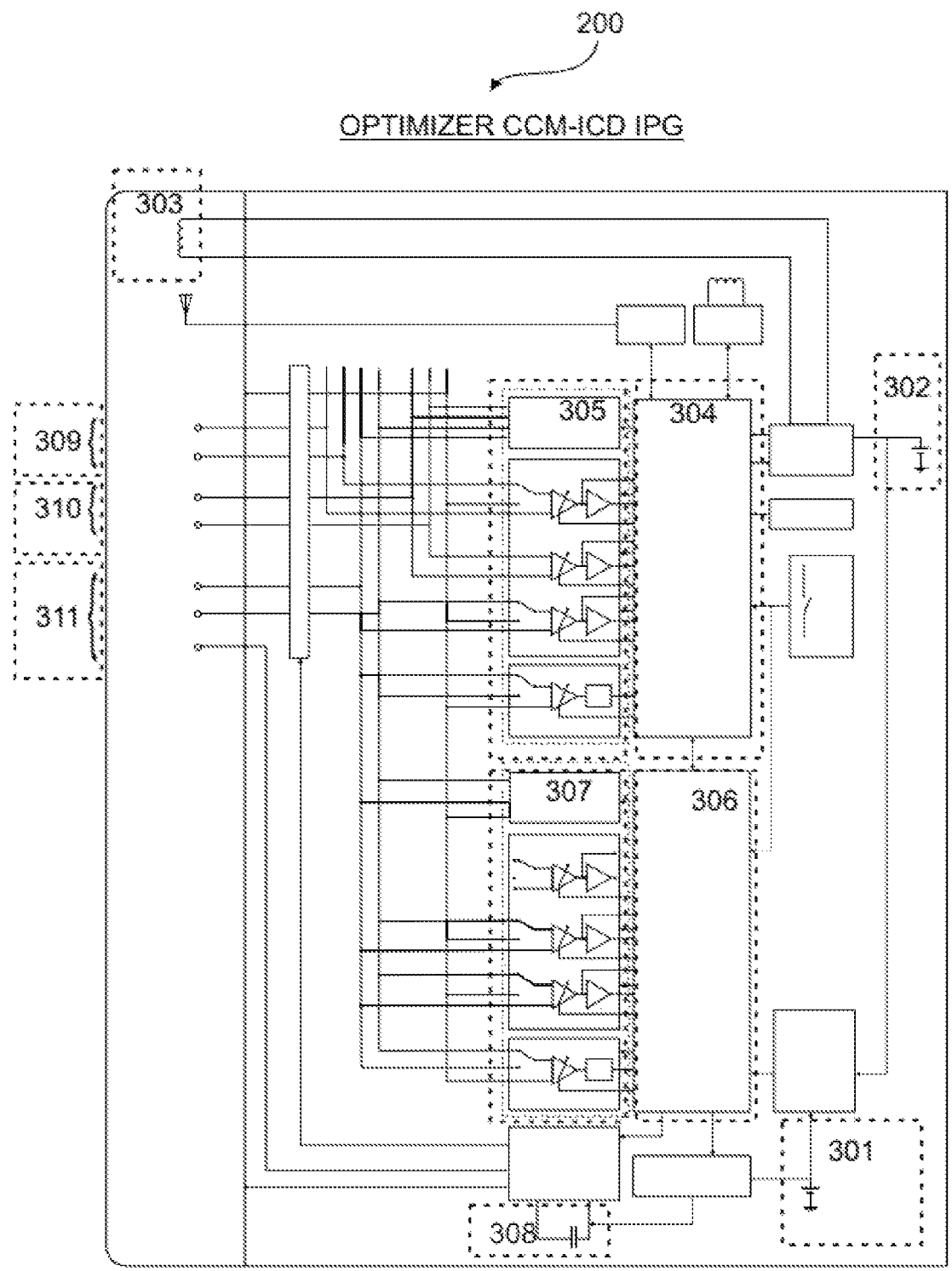
FIG. 3 is a simplified block diagram schematic illustration of an example embodiment of the invention.

Reference is now made to FIG. 3, which is a simplified block diagram schematic illustration of an example embodiment of the invention.

FIG. 3 shows a block diagram schematic illustration 300 of an example embodiment of the invention.

The example embodiment of FIG. 3 shows a simplified circuit illustration 300 of a Cardiac Contractility Modulation Implantable Cardioverter Defibrillator (ICD) device including:

a non-rechargeable battery 301;
a rechargeable battery 302;
an optional charging coil 303 for optionally charging the a rechargeable battery 302;
a Cardiac Contractility Modulation therapy and housekeeping micro-controller 304;
a Cardiac Contractility Modulation ASIC 305;
an ICD micro-controller 306;
a ICD ASIC 307;
a defibrillator capacitor 308; optional output(s) for a right atrium lead 309;
optional output(s) for a right ventricle lead 310; and
optional output(s) for a defibrillator lead 311.

Figure 4:
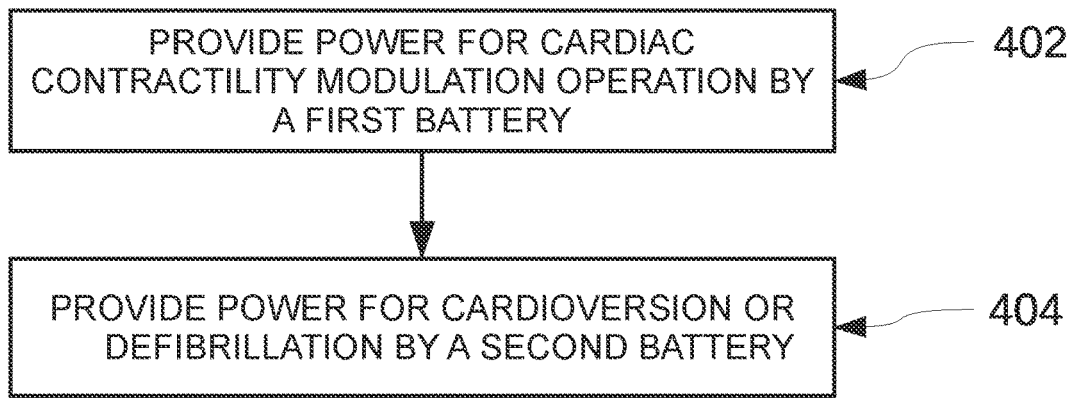
FIG. 4 is a simplified flow chart illustration of a method for providing power for a Cardiac Contractility Modulation Implantable Cardioverter Defibrillator (ICD) device according to an example embodiment of the invention.

Reference is now made to FIG. 4, which is a simplified flow chart illustration of a method for providing power for a Cardiac Contractility Modulation Implantable Cardioverter Defibrillator (ICD) device according to an example embodiment of the invention.

The method of FIG. 4 includes:
providing power for Cardiac Contractility Modulation operation by a first battery (402); and
providing power for cardioversion or defibrillation by a second battery (404).

In some embodiments, a micro-controller is used for sensing when the second battery cannot provide power for an operation powered by the second battery, and providing power from the first battery for the operation.

In some embodiments, the first battery is a non-rechargeable battery.

In some embodiments, the second battery is a rechargeable battery.

Figure 5:
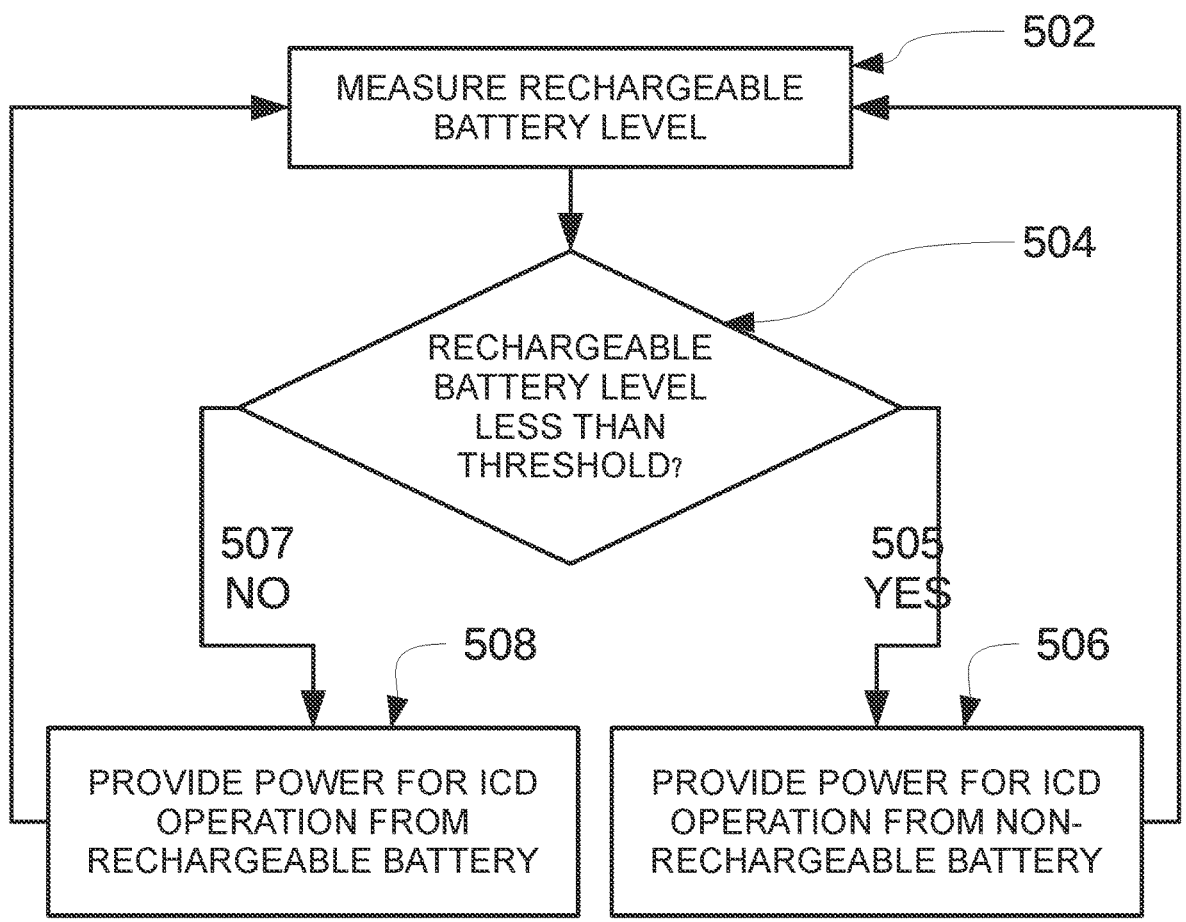
FIG. 5 is a simplified flow chart illustration of a method for controlling power for an Implantable Cardioverter Defibrillator (ICD) device according to an example embodiment of the invention.

Reference is now made to FIG. 5, which is a simplified flow chart illustration of a method for controlling power for an Implantable Cardioverter Defibrillator (ICD) device according to an example embodiment of the invention.

The method of FIG. 5 includes:
measuring electric power level of a rechargeable battery in the ICD (502);
comparing the rechargeable battery level to a threshold (504);
If the electric power level of the rechargeable battery is less than the threshold (505),
then providing power for the ICD from a non-rechargeable battery (506);
else providing power for the ICD from a rechargeable battery (507).

The method of FIG. 5 is suitable for use in controlling power in an ICD and for controlling power in an ICD which includes additional module configurations such as pacing, Cardiac Contractility Modulation stimulation, sensing, VT/VF detection, housekeeping, communications, operation of non-electric shock components in the implantable device, etc.

Figure 6A:
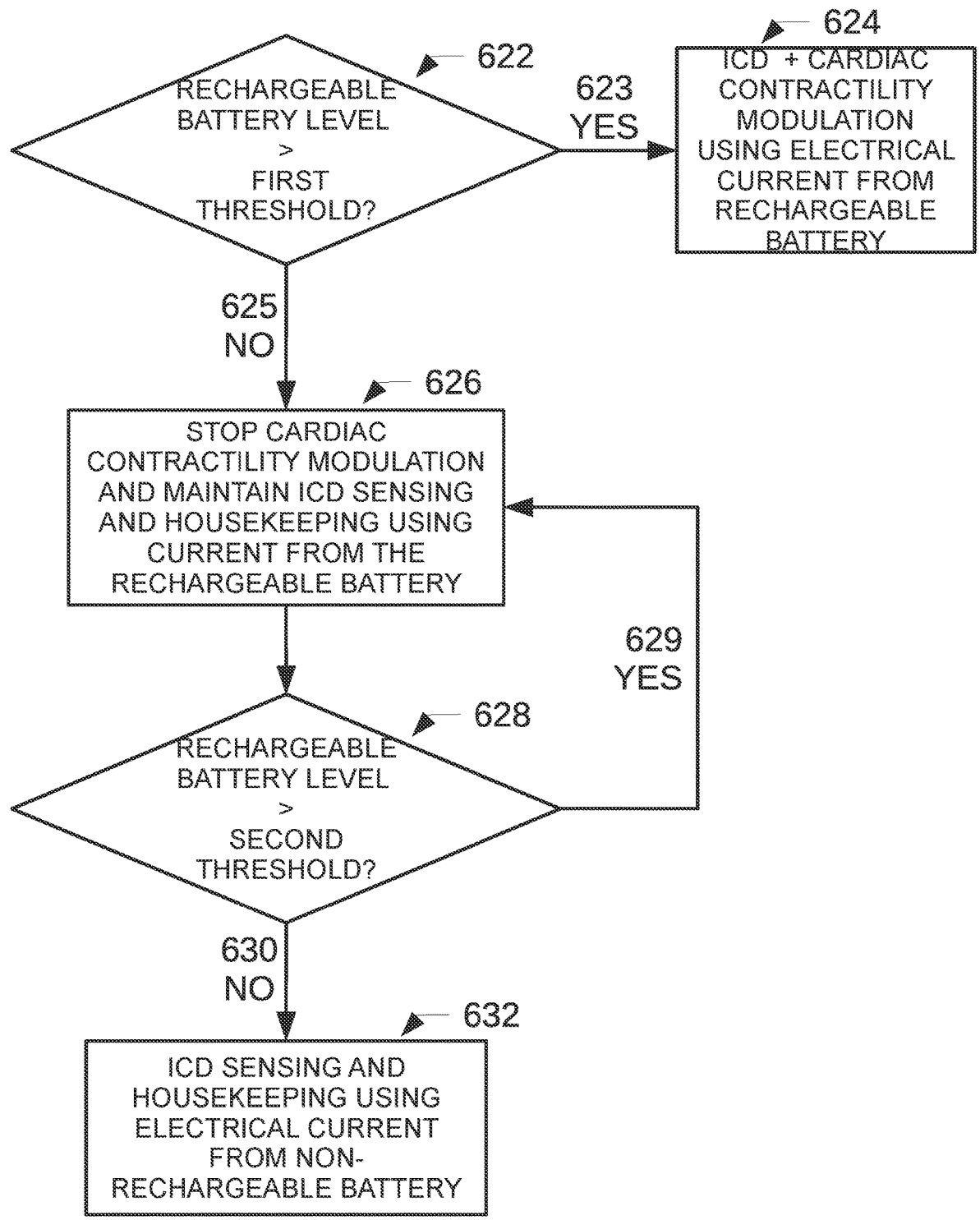
FIG. 6A is a simplified flow chart illustration of a method for controlling power for an Implantable Cardioverter Defibrillator (ICD) device according to an example embodiment of the invention.

Reference is now made to FIG. 6A, which is a simplified flow chart illustration of a method for controlling power for an Implantable Cardioverter Defibrillator (ICD) device according to an example embodiment of the invention.

The method of FIG. 6A includes:
comparing a rechargeable battery level to a first threshold (622);
if the electric power level of the rechargeable battery is greater than the first threshold (623), then continuing ICD sensing and housekeeping and Cardiac Contractility Modulation operation using electric current from the rechargeable battery (624); else
if the electric power level of the rechargeable battery is not greater than the first threshold (625), then stopping Cardiac Contractility Modulation operation and keeping ICD sensing and housekeeping using electric current from the rechargeable battery (626); and comparing the rechargeable battery level to a second threshold (628);

if the electric power level of the rechargeable battery is greater than the second threshold (629), then stopping Cardiac Contractility Modulation operation and maintaining ICD sensing and housekeeping using electric current from the rechargeable battery (626); and if the electric power level of the rechargeable battery is not greater than the second threshold (630), then performing ICD sensing and housekeeping using electric current from a non-rechargeable battery (632).

In some embodiments, the first threshold mentioned above with reference to FIG. 6A is greater than the second threshold mentioned above with reference to FIG. 6A.

In some embodiments, the first threshold and the second threshold mentioned above with reference to FIG. 6A are equal.

The method of FIG. 6A is suitable for use in controlling power in an ICD plus Cardiac Contractility Modulation configuration, for controlling power in an ICD plus pacemaker configuration, and for controlling power in an ICD which includes additional modules such as sensing, VT/VF detection, housekeeping, communications, operation of non-electric shock components in the implantable device, etc.

Figure 6B:
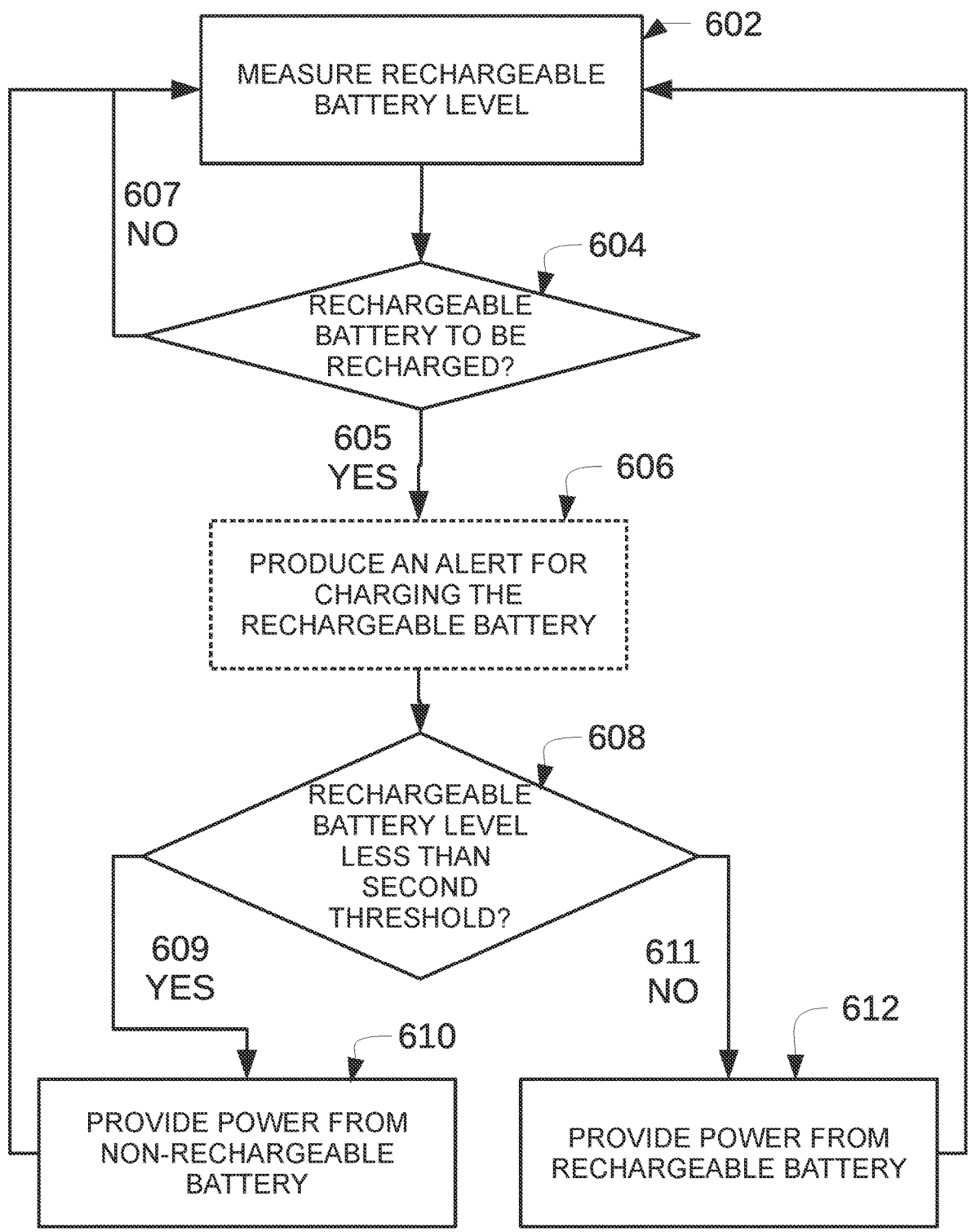
FIG. 6B is a simplified flow chart illustration of a method for controlling power for an Implantable Cardioverter Defibrillator (ICD) device according to an example embodiment of the invention.

Reference is now made to FIG. 6B, which is a simplified flow chart illustration of a method for controlling power for an Implantable Cardioverter Defibrillator (ICD) device according to an example embodiment of the invention.

The method of FIG. 6B includes:

measuring electric power level of a rechargeable battery in the ICD (602);

comparing the rechargeable battery level to a first threshold, to determine whether to recharge the rechargeable battery (604);

if the electric power level of the rechargeable battery is less than the threshold (605), then optionally producing an alert for charging the rechargeable battery (606);

comparing the rechargeable battery level to a second threshold (608), optionally for determining whether to switch providing power from the rechargeable battery to a non-rechargeable battery; and if the electric power level of the rechargeable battery is less than the second threshold (609), then switching providing power from the rechargeable battery to a non-rechargeable battery (610);

else continue providing power from the rechargeable battery (612).

In some embodiments, the first threshold mentioned above with reference to FIG. 6B is greater than the second threshold mentioned above with reference to FIG. 6B.

In some embodiments, the first threshold and the second threshold mentioned above with reference to FIG. 6B are equal.

The method of FIG. 6B is suitable for use in controlling power in an ICD, for controlling power in an ICD plus pacemaker configuration, and for controlling power in an ICD which includes additional modules such as Cardiac Contractility Modulation therapy, sensing, VT/VF detection, housekeeping, communications, operation of non-electric shock components in the implantable device, etc.

The method of FIG. 6B includes an optional step of producing an alert for charging the rechargeable battery. In some embodiments, the alert is optionally sent to a user interface.

Further descriptions of optionally producing alerts are described with reference to additional example embodiments of methods described below.

Reference is now made to FIG. 7, which is a simplified flow chart illustration of a method for controlling power for an ICD (Cardiac Contractility Modulation plus Implantable Cardioverter Defibrillator) device according to an example embodiment of the invention.

The method of FIG. 7 includes:

optionally checking that a rechargeable battery level is less than a first threshold (702);

if the electric power level of the rechargeable battery is not less than the first threshold (703) then continue device operation using the rechargeable battery (704), if the electric power level of the rechargeable battery is less than the first threshold (703) then, optionally setting a first alert for charging the rechargeable battery (706);

checking that the rechargeable battery level is greater than a second threshold (708);

if the electric power level of the rechargeable battery is greater than the second threshold (709) then continue device operation using the rechargeable battery (704), if the electric power level of the rechargeable battery is not greater than the second threshold (707) then, stopping operation of Cardiac Contractility Modulation treatment and keeping the ICD sensing and housekeeping using the rechargeable battery (710);

checking that the rechargeable battery level is greater than a third threshold (712);

if the electric power level of the rechargeable battery is greater than the third threshold (713) then stopping operation of Cardiac Contractility Modulation treatment and keeping the ICD operational using the rechargeable battery (710);

if the electric power level of the rechargeable battery is not greater than the third threshold (715) then providing power for ICD sensing and housekeeping using a non-rechargeable battery (716).

In some embodiments, the first threshold mentioned above with reference to FIG. 7 is greater than the second threshold mentioned above with reference to FIG. 7.

In some embodiments, the second threshold mentioned above with reference to FIG. 7 is greater than the third threshold mentioned above with reference to FIG. 7.

In some embodiments, two or more of the first threshold, the second threshold, and the third threshold mentioned above with reference to FIG. 7 are equal.

In some embodiments if the electric power level of the rechargeable battery is not greater than the second threshold (707) then optionally producing a second alert. The second alert optionally indicates that operation of Cardiac Contractility Modulation treatment has been stopped, potentially indicating urgency to recharging the rechargeable battery.

In some embodiments, if the electric power level of the rechargeable battery is not greater than the third threshold (715) then optionally producing a third alert. The third alert optionally indicates that operation of ICD has been switched to the non-rechargeable battery, potentially indicating urgency to recharging the rechargeable battery.

The method of FIG. 7 is suitable for use in controlling power in an ICD, for controlling power in an ICD plus Cardiac Contractility Modulation configuration, and for controlling power in an ICD which includes additional module configurations such as a pacemaker, sensing, VT/VF detection, housekeeping, communications, operation of non-electric shock components in the implantable device, etc.

Reference is now made to FIG. 8, which is a simplified flow chart illustration of a method for controlling power for an ICD plus a sensing and/or monitoring configuration according to an example embodiment of the invention.

The method of FIG. 8 includes:
checking whether a rechargeable battery level is greater than a first threshold (802);
if the electric power level of the rechargeable battery is greater than the first threshold (803) then continuing device operation using the rechargeable battery (804);
if the electric power level of the rechargeable battery is not greater than the first threshold (805) then,
  optionally setting a first alert for charging the rechargeable battery (806);
  checking that the rechargeable battery level is greater than a second threshold (808);
  if the electric power level of the rechargeable battery is greater than the second threshold (809) then continuing device operation using the rechargeable battery (804);
  if the electric power level of the rechargeable battery is not greater than the second threshold (811) then optionally setting a second alert (812);
    stopping operation of non-ICD module(s) and maintaining the ICD sensing and housekeeping using the rechargeable battery (814);
    checking that the rechargeable battery level is less than a third threshold (816);
    if the electric power level of the rechargeable battery is less than the third threshold (817) then providing power for ICD sensing and housekeeping using a non-rechargeable battery (818);
    if the electric power level of the rechargeable battery is not less than the third threshold (819) then maintaining the ICD sensing and housekeeping using the rechargeable battery (814).

In some embodiments, the first threshold mentioned above with reference to FIG. 8 is greater than the second threshold mentioned above with reference to FIG. 8.

In some embodiments, the second threshold mentioned above with reference to FIG. 8 is greater than the third threshold mentioned above with reference to FIG. 8.

In some embodiments, two or more of the first threshold, the second threshold, and the third threshold mentioned above with reference to FIG. 8 are equal.

In some embodiments, once the alerts are set, the alerts stay on until explicitly turned off, possibly after recharging the rechargeable battery.

The method of FIG. 8 is suitable for use in controlling power in an ICD, for controlling power in an ICD plus a sensing and/or monitoring configuration.

In some embodiments, the second alert optionally indicates that operation of non-ICD operations has been stopped, potentially indicating urgency to recharging the rechargeable battery.

In some embodiments, if the electric power level of the rechargeable battery is less than the third threshold (817) then optionally producing a third alert. The third alert optionally indicates that operation of ICD has been switched to the non-rechargeable battery, potentially indicating urgency to recharging the rechargeable battery.

It is expected that during the life of a patent maturing from this application many relevant batteries will be developed and the scope of the term battery is intended to include all such new technologies a priori.

It is expected that during the life of a patent maturing from this application many relevant implantable devices will be developed and the scope of the term implantable device is intended to include all such new technologies a priori.

As used herein with reference to quantity or value, the term "about" means "within ±25% of".

The terms "comprising", "including", "having" and their conjugates mean "including but not limited to".

The term "consisting of" is intended to mean "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a unit" or "at least one unit" may include a plurality of units, including combinations thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. An implantable device containing a plurality of batteries, the plurality of batteries comprising:
    at least one first non-rechargeable battery;
    at least one second rechargeable battery;
    an Implantable Cardioverter Defibrillator (ICD) unit;
    a Cardiac Contractility Modulation unit; and
    a controller,
    wherein the controller is configured to:
        provide power for life-saving function operation by a first, non-rechargeable battery;
        provide power for non-life-saving function operation by a second, rechargeable battery;
        measure an electric power level of the rechargeable battery; and
        compare the rechargeable battery level to a first threshold;
        if the electric power level of the rechargeable battery is less than the first threshold, then sustain ICD module operation using electric current from the rechargeable battery and not sustain Cardiac Contractility Modulation operation; and
        compare the rechargeable battery level to a second threshold, wherein if the electric power level of the rechargeable battery is less than the second threshold then sustain the ICD module operation using electric current from the non-rechargeable battery.

2. The device of claim 1, wherein the non-life-saving function comprises Non-excitatory Electrical Signals (NES), synchronized with electrical action in a cardiac cycle.

3. The device of claim 1, wherein the non-life-saving function comprises Cardiac Contractility Modulation.

4. The device of claim 1, wherein the life-saving function comprises cardioversion or defibrillation.

5. The device of claim 1, wherein the implantable device comprises an Implantable Cardioversion Device (ICD).

6. The device of claim 1, wherein the implantable device is configured to deliver cardiac pacing powered by the second rechargeable battery.

7. The device of claim 1, wherein the first threshold is at a higher level than the second threshold.

8. The device of claim 1, wherein the first threshold is equal to the second threshold.

9. The device of claim 1, wherein if the electric power level of the rechargeable battery is less than the first threshold then setting an alert to recharge the rechargeable battery.

10. The device of claim 1, wherein the controller is configured to sense when the second, rechargeable battery cannot provide power for an operation powered by the second, rechargeable battery and provide power from the first, non-rechargeable battery for the operation.

11. The device of claim 1, wherein the controller is configured to:
    measure an electric power level of the rechargeable battery;
    compare the level of the rechargeable battery to a first threshold;
    if the electric power level of the rechargeable battery is less than the threshold then stop Cardiac Contractility Modulation stimulation, and use energy from the rechargeable battery for Cardioverter Defibrillator sensing and housekeeping;
    and
    compare the level of the rechargeable battery to a second threshold,
    wherein if the electric power level of the rechargeable battery is less than the second threshold, then provide power for Cardioverter Defibrillator operation from the non-rechargeable battery.

12. The device of claim 11, wherein if the electric power level of the rechargeable battery is less than a third threshold then setting an alert to recharge the rechargeable battery.

13. The device of claim 12, wherein the third threshold is at a higher level than the first threshold.

* * * * *